(12) United States Patent
Al-Ali et al.

(10) Patent No.: US 7,880,626 B2
(45) Date of Patent: Feb. 1, 2011

(54) SYSTEM AND METHOD FOR MONITORING THE LIFE OF A PHYSIOLOGICAL SENSOR

(75) Inventors: Ammar Al-Ali, Tustin, CA (US); Walter M. Weber, Laguna Hills, CA (US); Ryan Timothy McHale, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 735 days.

(21) Appl. No.: 11/580,214

(22) Filed: Oct. 12, 2006

(65) Prior Publication Data

US 2008/0088467 A1    Apr. 17, 2008

(51) Int. Cl.
G08B 21/00    (2006.01)
A61B 5/00    (2006.01)

(52) U.S. Cl. .................... 340/635; 340/636.19; 600/323

(58) Field of Classification Search .............. 340/636.1, 340/636.11–636.19; 600/323
See application file for complete search history.

(56) References Cited

U.S. PATENT DOCUMENTS

| | | | |
|---|---|---|---|
| 4,815,469 A * | 3/1989 | Cohen et al. ................. | 600/333 |
| 4,858,615 A * | 8/1989 | Meinema .................... | 600/481 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,317,269 A * | 5/1994 | Mills et al. .................. | 324/427 |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |

(Continued)

FOREIGN PATENT DOCUMENTS

WO     WO 02/17779 A1     3/2002
WO  PCT/US2007/081146     11/2008

OTHER PUBLICATIONS

PCT International Search Report for International Application No. PCT/US2007/081146, Mailing Date of May 21, 2008, in 6 pages.

*Primary Examiner*—Jennifer Mehmood
(74) *Attorney, Agent, or Firm*—Knobbe Martens Olson & Bear, LLP

(57) ABSTRACT

Aspects of the present disclosure include a sensor configured to store in memory indications of sensor use information and formulas or indications of formula for determining the useful life of a sensor from the indications of sensor use information. A monitor connected to the sensor monitors sensor use and stores indications of the use on sensor memory. The monitor and/or sensor use the compute the useful life of the sensor from the indications of use and the formulas. When the useful life of the sensor is reached, an indication is given to replace the sensor.

33 Claims, 9 Drawing Sheets

U.S. PATENT DOCUMENTS

| | | | |
|---|---|---|---|
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,991,355 A * | 11/1999 | Dahlke | 377/15 |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,321,100 B1 | 11/2001 | Parker | |
| 6,330,468 B1 * | 12/2001 | Scharf | 600/476 |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,433,696 B1 * | 8/2002 | Deiterman et al. | 340/632 |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,553,241 B2 * | 4/2003 | Mannheimer et al. | 600/323 |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,997,879 B1 * | 2/2006 | Turcott | 600/507 |
| 6,999,904 B2 | 2/2006 | Weber et al. | |
| 7,003,338 B2 | 2/2006 | Weber et al. | |

| | | |
|---|---|---|
| 7,003,339 B2 | 2/2006 | Diab et al. |
| 7,015,451 B2 | 3/2006 | Dalke et al. |
| 7,024,233 B2 | 4/2006 | Al et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,248,910 B2 | 7/2007 | Luya Li et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,660,616 B1 * | 2/2010 | Poore .................. 600/341 |
| 2002/0013538 A1* | 1/2002 | Teller .................. 600/549 |
| 2003/0111592 A1 | 6/2003 | Ammar Al-Ali |
| 2004/0267103 A1* | 12/2004 | Li et al. .................. 600/323 |
| 2005/0221276 A1* | 10/2005 | Rozakis et al. .................. 435/4 |
| 2005/0234317 A1* | 10/2005 | Kiani .................. 600/323 |
| 2006/0161054 A1 | 7/2006 | Reuss et al. |
| 2006/0167351 A1* | 7/2006 | Isaacson et al. .................. 600/323 |
| 2006/0220879 A1* | 10/2006 | Chan .................. 340/573.1 |

\* cited by examiner

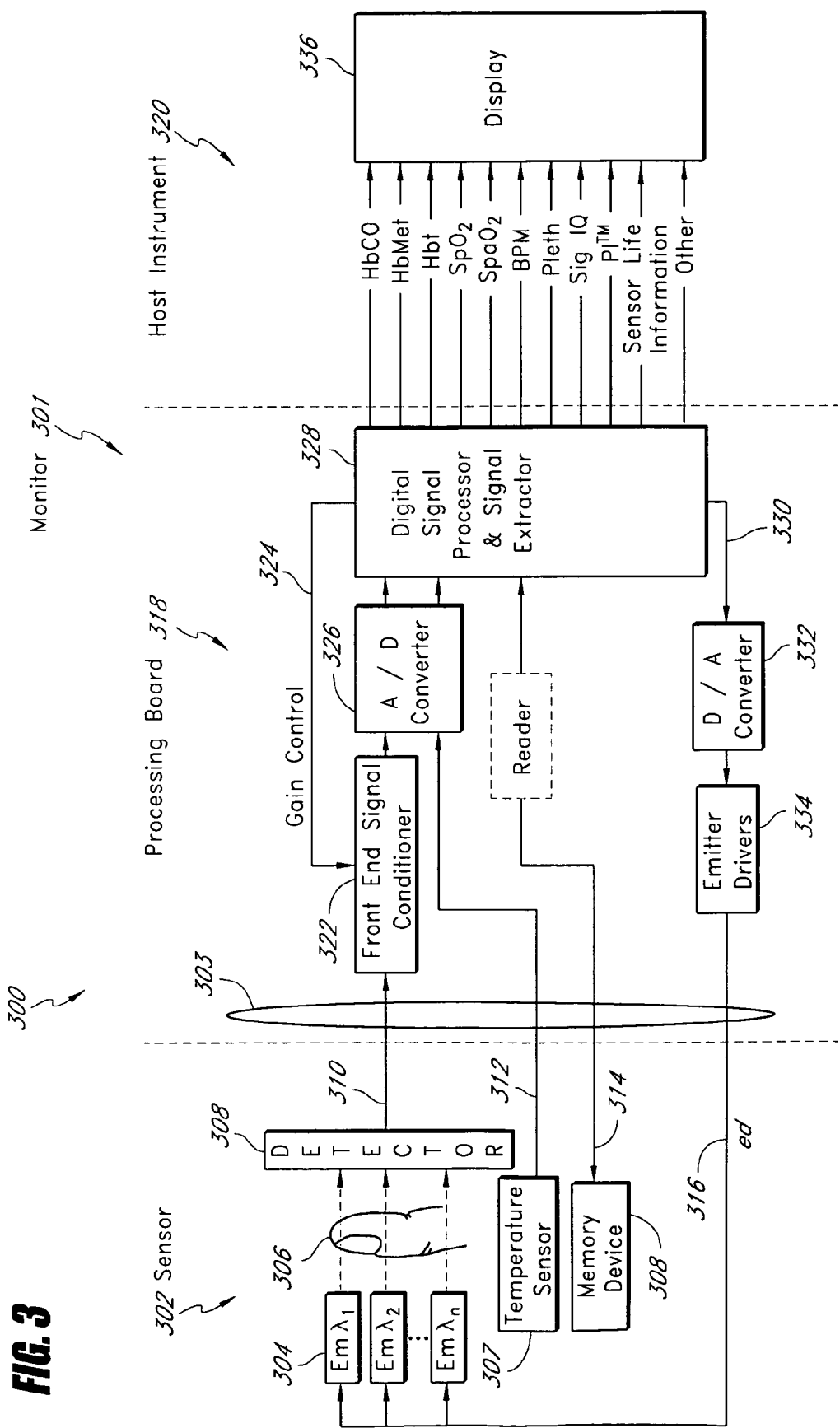

SYSTEM AND METHOD FOR MONITORING THE LIFE OF A PHYSIOLOGICAL SENSOR

CROSS REFERENCE TO RELATED APPLICATIONS

The present invention relates to U.S. Pat. No. 6,388,240, filed Mar. 2, 2001, entitled "Shielded Optical Probe and Method Having a Longevity Indication," and U.S. Pat. No. 6,515,273, filed Feb. 10, 2000, entitled "A system for Indicating the Expiration of the Useful Operating Life of a Pulse Oximetry Sensor," their continuations, divisionals, continuation-in-parts and the like, and incorporates each of the foregoing disclosures herein by reference.

FIELD OF THE INVENTION

The present invention relates to a sensor for measuring oxygen content in the blood, and, in particular, relates to an apparatus and method for monitoring the life of a pulse oximetry sensor.

BACKGROUND

Early detection of low blood oxygen is critical in a wide variety of medical applications. For example, when a patient receives an insufficient supply of oxygen in critical care and surgical applications, brain damage and death can result in just a matter of minutes. Because of this danger, the medical industry developed pulse oximetry, a noninvasive procedure for measuring the oxygen saturation of the blood. A pulse oximeter interprets signals from a sensor attached to a patient in order to determine that patient's blood oxygen saturation.

A conventional pulse oximetry sensor has a red emitter, an infrared emitter, and a photodiode detector. The sensor is typically attached to a patient's finger, earlobe, or foot. For a finger, the sensor is configured so that the emitters project light from one side of the finger, through the outer tissue of the finger, and into the blood vessels and capillaries contained inside. The photodiode is positioned at the opposite side of the finger to detect the emitted light as it emerges from the outer tissues of the finger. The photodiode generates a signal based on the emitted light and relays that signal to the pulse oximeter. The pulse oximeter determines blood oxygen saturation by computing the differential absorption by the arterial blood of the two wavelengths (red and infrared) emitted by the sensor.

The foregoing conventional sensor is typically detachable from the oximeter to allow for periodic replacement. Periodic replacement is advantageous for a wide variety of reasons. For example, the sensor can become soiled, thereby possibly inhibiting sensor sensitivity or causing cross-patient contamination. Furthermore, the electronic circuitry in the sensor can become damaged, thereby causing sensor failure or inaccurate results. Moreover, the securing mechanism for the sensor, such as an adhesive substrate, can begin to fail, thereby improperly positioning the sensor in proximity to a measurement site and providing inaccurate data. Accordingly, periodic replacement of the sensor is an important aspect of maintaining a sterile, highly sensitive, accurate pulse oximetry system.

However, a conventional pulse oximetry sensor is generally reliant on an operator for timely replacement of soiled, damaged, or otherwise overused sensors. This approach is problematic not only from the standpoint of operator mistake or negligence, but also from the perspective of deliberate misuse for cost saving or other purposes.

SUMMARY

Accordingly, one aspect of the present invention is to provide an inexpensive, accurate sensor life monitoring system for monitoring the useful and safe life of a pulse oximetry sensor. In an embodiment, a sensor is provided with a memory device, such as, for example, an EPROM or EEPROM. At predetermined intervals and/or in response to predetermined events, information is written onto the memory device. When the sensor reaches a predetermined level of use, a sensor replacement signal is indicated to a user.

In an embodiment, depending on the characteristics of the sensor, the sensor stores information related to the life expectancy of the sensor. In an embodiment, the life expectancy information is a function or set of functions that is used to calculate the useful life of the sensor. In an embodiment, the information is an indication of the use of the sensor. In an embodiment, the function or set of functions is stored on the sensor with an indication of the use of the sensor. In an embodiment, the function or set of functions is used in conjunction with the indication of the use of the sensor in order to determine the useful life of the sensor.

In an embodiment, the function or set of functions is a predetermined function or set of functions based on empirical data obtained from observing sensor use and/or inspecting used sensors. In an embodiment the empirical data is obtained experimentally in the normal course of using a sensor on a patient. In an embodiment, the empirical data is obtained experimentally without using patients. In an embodiment, the function or set of functions is based on theoretical data. In an embodiment, the function or set of functions is based on the individual life of each component of the sensor.

In an embodiment, a patient monitor works in conjunction with the sensor to determine the useful life of the sensor. In an embodiment, the monitor tracks information related to the use of the sensor and stores an indication of the information related to the use on the sensor. In an embodiment, the monitor uses the information stored on the sensor, including the functions and/or the previously stored indications of use and calculates the useful sensor life. In an embodiment, the monitor updates the already stored indications of use on the sensor. In an embodiment, the monitor indicates a sensor life expired status to a user.

In an embodiment, the sensor uses the function(s) and/or the indications of use and calculates the useful sensor life. In an embodiment, the sensor calculates the useful life of the sensor based on information provided by the monitor. In an embodiment, the monitor stores the functions and or the sensor use information relevant to a particular sensor. In an embodiment, a range or set of functions is stored on the monitor and the sensor stores an indication of which function or set of functions are to be used to calculate the useful life of the sensor. In an embodiment, indications of use information are stored on the sensor, so as to conserve memory space. In an embodiment, the sensor memory includes both read only and read/write memory. In an embodiment, the read only memory stores the functions and other read only information such as the update period, expiration limit, index of functions, near expiration percentage, or the like. In an embodiment, the read/write memory stores use information which changes periodically based on the use of the sensor.

In an embodiment, the use information includes one or more of the following: the number of times a sensor has been connected and/or disconnected from a monitor, the number of times the sensor has been successfully calibrated, the total elapsed time the sensor has been connected to the monitor, the total time the sensor has been used to process the patient vital parameters, the age of the sensor, the cumulative or average current applied to the LED's, the cumulative or average current provided to the sensor, the cumulative or average temperature of the sensor during use, an indication of the expiration status or existing life of the sensor, the number of times the clip has been depressed, the number of times the clip has been placed on a patient, the number patients the sensor has been used on, the number of times and time between cleanings and/or sterilization of the sensor, the number of monitors a particular sensor has been connected to, the number of times a sensor has been refurbished, the number of times the sensor has been sterilized, the time period between uses, as well as any other information useful in determining the life of a sensor as would be understood by a person of ordinary skill in the art from the disclosure herein.

In an embodiment, a reusable noninvasive physiological sensor is disclosed. The sensor has a first and second emitter which emit light of at least two wavelengths through tissue, a detector which senses the light after it has passed through the tissue and generates a signal indicative of the sensed light, a memory device which stores an indication of sensor use information and an indication of a function to be used in determining the useful life of the sensor, and a communication port which communicates at least the signal and information stored on the memory with a patient monitor. In an embodiment, the memory device has a read only portion and a read/write portion. In an embodiment, the indication of the function is stored in the read only portion and the indication of sensor use information is stored in the read/write portion of the memory. In an embodiment, the memory device is made up of a plurality of memory devices. In an embodiment, the indication of the sensor use information is an indication of one or more of an age of the sensor, a use time of the sensor, a current supplied to the sensor, a temperature of the sensor, a number of times the sensor is depressed, a number of times the sensor is calibrated, or a number of times the sensor is powered up. In an embodiment, the monitor tracks the use information and sends an indication of the use information to the sensor for storage in the memory.

In an embodiment, a method of determining the useful life of a physiological sensor is disclosed, the method includes the steps of using a physiological sensor having a memory device to obtain physiological information, monitoring the use of the sensor, storing an indication of the use of the sensor on the memory device, and determining when the useful life of the sensor has been exceeded by using a mathematical function and the indications of use. In an embodiment, the indication of the use of the sensor includes an indication of one or more of an age of the sensor, a use time of the sensor, a current supplied to the sensor, a temperature of the sensor, a number of times the sensor is depressed, a number of times the sensor is calibrated, or a number of times the sensor is powered up. In an embodiment, the step of monitoring the use of the sensor is performed by a patient monitor. In an embodiment, the step of monitoring the use of the sensor is performed by the sensor. In an embodiment, the mathematical function is stored in the sensor memory. In an embodiment, the mathematical function is stored in the memory of a patient monitor. In an embodiment, an indication of the mathematical function is stored in the sensor memory. In an embodiment, the mathematical function is derived from use data. In an embodiment, the use data is obtained from used sensors. In an embodiment, the used sensors have been used on patients. In an embodiment, the physiological sensor is one or more of a blood oxygen sensor, a blood pressure sensor, or an ECG sensor.

In an embodiment, a method of reusing at least portion of a sensor is disclosed. The method includes the steps of accessing a memory device of a physiological sensor, retrieving sensor use information on the memory device, and using the retrieved sensor use information determine if at least one portion of the sensor can be reused. In an embodiment, the method also includes the step of reusing at least one portion of the sensor. In an embodiment, the step of reusing includes producing a refurbished sensor including at least one part of the sensor. In an embodiment, the method also includes the step of analyzing the use information to determine an extent of use of the sensor. In an embodiment, the method includes the step of storing reuse information on the refurbished sensor.

In an embodiment, a method of indicating when a physiological sensor needs to be replaced is disclosed. The method includes the steps of emitting light from a light emitting element, detecting light from the light emitting element after it has been attenuated by tissue, storing information on a sensor memory module, determining when the sensor memory module is full, and indicating that the sensor needs be replaced when it is determined that the sensor memory module is full. In an embodiment, the method includes the step of storing information at predetermined time intervals. In an embodiment, the information includes usage information.

BRIEF DESCRIPTION OF THE DRAWINGS

FIG. 3 illustrates a block diagram of an exemplary embodiment of a monitoring system.

DETAILED DESCRIPTION

Figure 1:
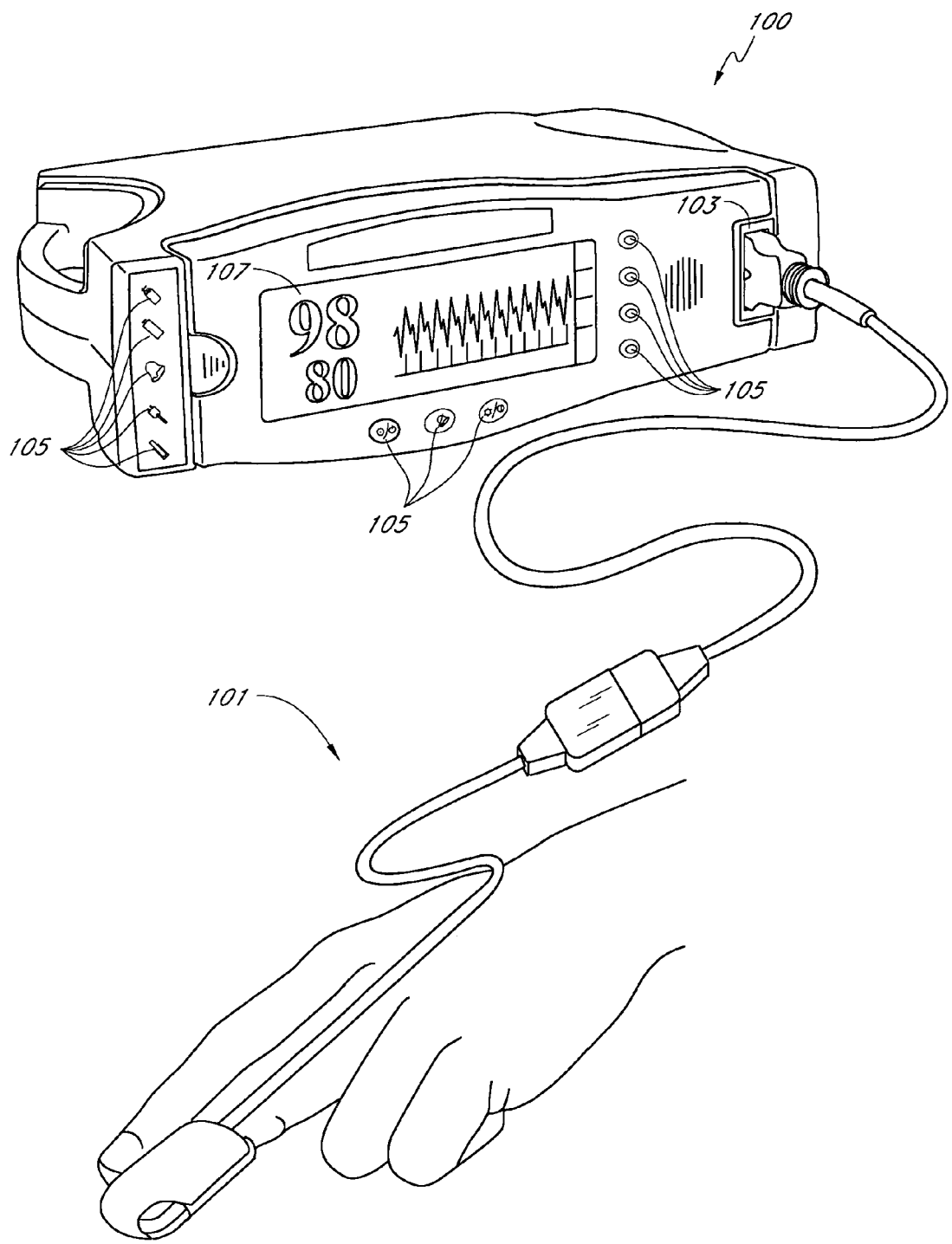
FIG. 1 illustrates an embodiment of a physiological measurement system.

FIG. 1 illustrates an embodiment of a physiological measurement system 100 having a monitor 101 and a sensor assembly 101. The physiological measurement system 100 allows the monitoring of a person, including a patient. In particular, the multiple wavelength sensor assembly 101 allows the measurement of blood constituents and related parameters, including oxygen saturation, HbCO, HBMet and pulse rate.

In an embodiment, the sensor assembly 101 is configured to plug into a monitor sensor port 103. Monitor keys 105 provide control over operating modes and alarms, to name a few. A display 107 provides readouts of measured parameters, such as oxygen saturation, pulse rate, HbCO and HbMet to name a few.

Figure 2A:
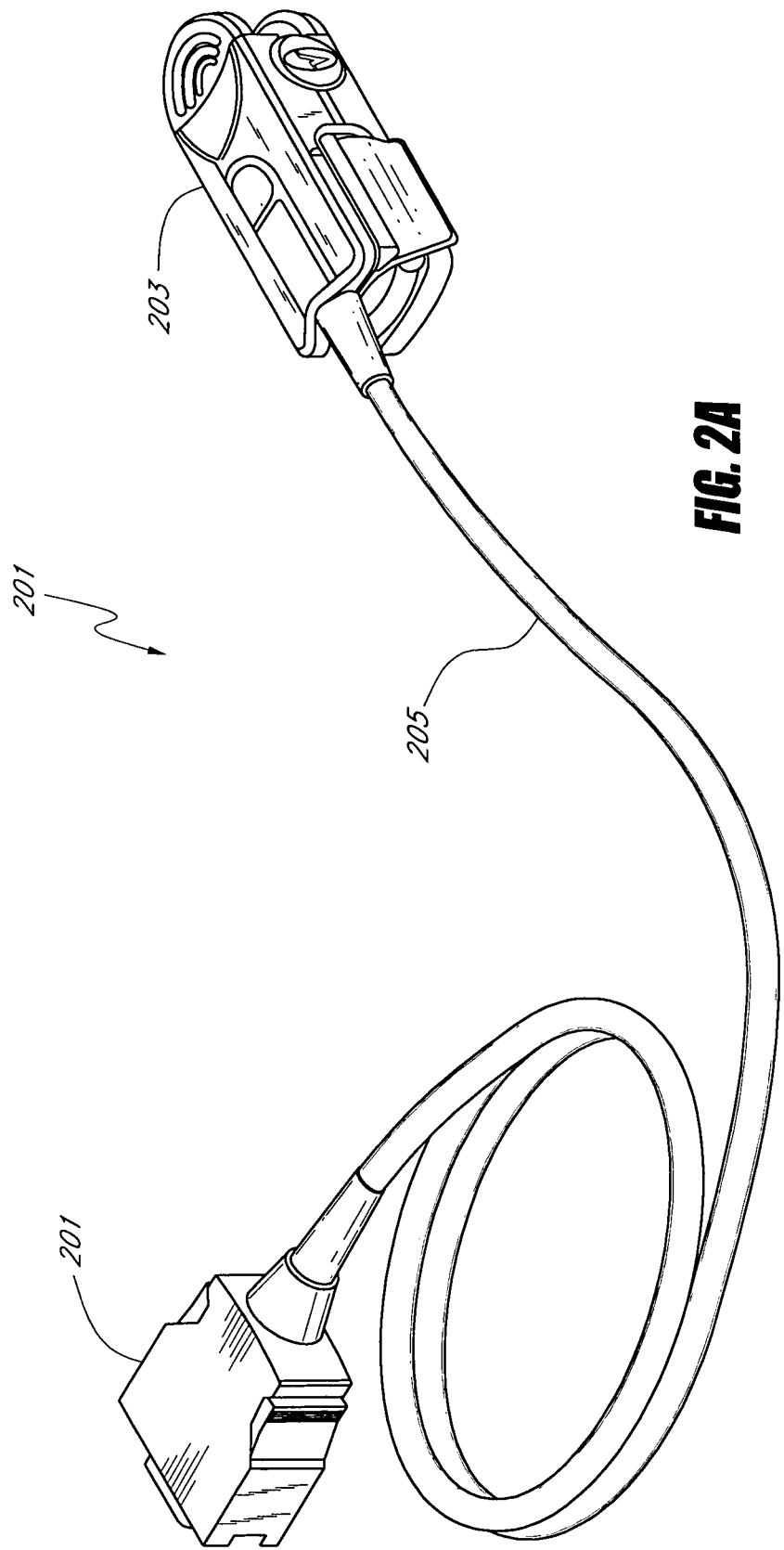
FIG. 2A illustrates an embodiment of a sensor assembly.

FIG. 2A illustrates a multiple wavelength sensor assembly 201 having a sensor 203 adapted to attach to a tissue site, a sensor cable 205 and a monitor connector 201. In an embodiment, the sensor 203 is incorporated into a reusable finger clip adapted to removably attach to, and transmit light through, a fingertip. The sensor cable 205 and monitor connector 201 are integral to the sensor 203, as shown. In alternative embodiments, the sensor 203 can be configured separately from the cable 205 and connector 201, although such communication can advantageously be wireless, over public or private networks or computing systems or devices, through intermediate medical or other devices, combinations of the same, or the like.

Figure 2B:
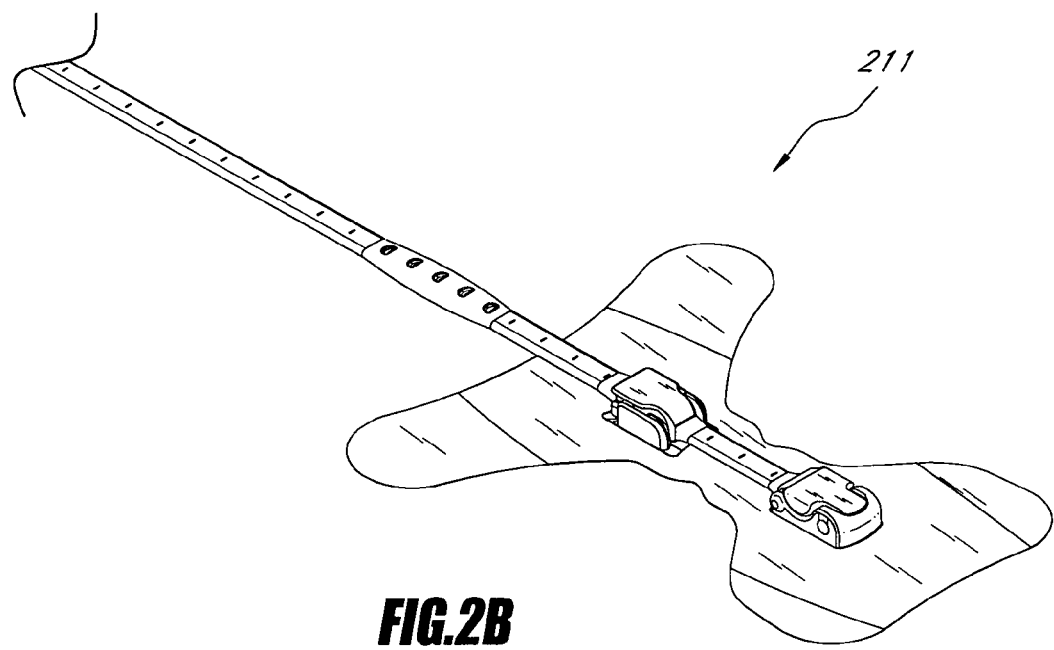
FIGS. 2B-C illustrate alternative sensor embodiments.
Figure 2C:
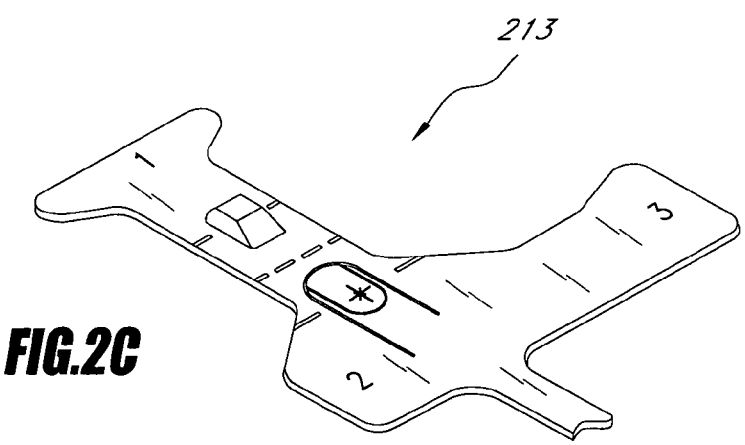

FIGS. 2B-C illustrate alternative sensor embodiments, including a sensor 211 (FIG. 2B) partially disposable and partially reusable (resposable) and utilizing an adhesive attachment mechanism. Also shown is a sensor 213 being disposable and utilizing an adhesive attachment mechanism. In other embodiments, a sensor can be configured to attach to various tissue sites other than a finger, such as a foot or an ear. Also a sensor can be configured as a reflectance or transflectance device that attaches to a forehead or other tissue surface. The artisan will recognize from the disclosure herein that the sensor can include mechanical structures, adhesive or other tape structures, Velcro wraps or combination structures specialized for the type of patient, type of monitoring, type of monitor, or the like.

FIG. 3 illustrates a block diagram of an exemplary embodiment of a monitoring system 300. As shown in FIG. 3, the monitoring system 300 includes a monitor 301, a noninvasive sensor 302, communicating through a cable 303. In an embodiment, the sensor 302 includes a plurality of emitters 304 irradiating the body tissue 306 with light, and one or more detectors 308 capable of detecting the light after attenuation by tissue 306. As shown in FIG. 3, the sensor 302 also includes a temperature sensor 307, such as, for example, a thermistor or the like. The sensor 302 also includes a memory device 308 such as, for example, an EEPROM, EPROM or the like. The sensor 302 also includes a plurality of conductors communicating signals to and from its components, including detector composite signal conductors 310, temperature sensor conductors 312, memory device conductors 314, and emitter drive signal conductors 316.

According to an embodiment, the sensor conductors 310, 312, 314, 316 communicate their signals to the monitor 301 through the cable 303. Although disclosed with reference to the cable 303, a skilled artisan will recognize from the disclosure herein that the communication to and from the sensor 306 can advantageously include a wide variety of cables, cable designs, public or private communication networks or computing systems, wired or wireless communications (such as Bluetooth or WiFi, including IEEE 801.11a, b, or g), mobile communications, combinations of the same, or the like. In addition, communication can occur over a single wire or channel or multiple wires or channels.

In an embodiment, the temperature sensor 307 monitors the temperature of the sensor 302 and its components, such as, for, example, the emitters 304. For example, in an embodiment, the temperature sensor 307 includes or communicates with a thermal bulk mass having sufficient thermal conduction to generally approximate a real-time temperature of a substrate of the light emission devices 304. The foregoing approximation can advantageously account for the changes in surface temperature of components of the sensor 302, which can change as much or more than ten degrees Celsius (10° C.) when the sensor 302 is applied to the body tissue 306. In an embodiment, the monitor 101 can advantageously use the temperature sensor 307 output to, among other things, ensure patient safety, especially in applications with sensitive tissue. In an embodiment, the monitor 301 can advantageously use the temperature sensor 307 output and monitored operating current or voltages to correct for operating conditions of the sensor 302 as described in U.S. patent application Ser. No. 11/366,209, filed Mar. 1, 2006, entitled "Multiple Wavelength Sensor Substrate," and herein incorporated by reference.

The memory 308 can include any one or more of a wide variety of memory devices known to an artisan from the disclosure herein, including an EPROM, an EEPROM, a flash memory, a combination of the same or the like. The memory 308 can include a read-only device such as a ROM, a read and write device such as a RAM, combinations of the same, or the like. The remainder of the present disclosure will refer to such combination as simply EPROM for ease of disclosure; however, an artisan will recognize from the disclosure herein that the memory 308 can include the ROM, the RAM, single wire memories, combinations, or the like.

The memory device 308 can advantageously store some or all of a wide variety data and information, including, for example, information on the type or operation of the sensor 302, type of patient or body tissue 306, buyer or manufacturer information, sensor characteristics including the number of wavelengths capable of being emitted, emitter specifications, emitter drive requirements, demodulation data, calculation mode data, calibration data, software such as scripts, executable code, or the like, sensor electronic elements, sensor life data indicating whether some or all sensor components have expired and should be replaced, encryption information, monitor or algorithm upgrade instructions or data, or the like. In an embodiment, the memory device 308 can also include emitter wavelength correction data.

In an advantageous embodiment, the monitor reads the memory device on the sensor to determine one, some or all of a wide variety of data and information, including, for example, information on the type or operation of the sensor, a type of patient, type or identification of sensor buyer, sensor manufacturer information, sensor characteristics including the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters it is intended to measure (e.g., HbCO, HbMet, etc.) calibration data, software such as scripts, executable code, or the like, sensor electronic elements, whether it is a disposable, reusable, or multi-site partially reusable, partially disposable sensor, whether it is an adhesive or non-adhesive sensor, whether it is reflectance or transmittance sensor, whether it is a finger, hand, foot, forehead, or ear sensor, whether it is a stereo sensor or a two-headed sensor, sensor life data indicating whether some or all sensor components have expired and should be replaced, encryption information, keys, indexes to keys or has functions, or the like monitor or algorithm upgrade instructions or data, some or all of parameter equations, information about the patient, age, sex, medications, and other information that can be useful for the accuracy or alarm settings and sensitivities, trend history, alarm history, sensor life, or the like.

FIG. 3 also shows the monitor 301 comprising one or more processing boards 318 communicating with one or more host instruments 320. According to an embodiment, the board 318 includes processing circuitry arranged on one or more printed circuit boards capable of installation into the handheld or other monitor 301, or capable of being distributed as an OEM component for a wide variety of host instruments 320 monitoring a wide variety of patient information, or on a separate unit wirelessly communicating to it. As shown in FIG. 3, the board 318 includes a front end signal conditioner 322 including an input receiving the analog detector composite signal from the detector 308, and an input from a gain control signal 324. The signal conditioner 322 includes one or more outputs communicating with an analog-to-digital converter 326 ("A/D converter 326").

The A/D converter 326 includes inputs communicating with the output of the front end signal conditioner 322 and the output of the temperature sensor 307. The converter 326 also includes outputs communicating with a digital signal processor and signal extractor 328. The processor 328 generally communicates with the A/D converter 326 and outputs the gain control signal 324 and an emitter driver current control signal 330. The processor 328 also communicates with the memory device 308. As shown in phantom, the processor 328 can use a memory reader, memory writer, or the like to communicate with the memory device 308. Moreover, FIG. 3 also shows that the processor 328 communicates with the host instrument 320 to for example, display the measured and calculated parameters or other data.

FIG. 3 also shows the board 318 including a digital-to-analog converter 332 ("D/A converter 332") receiving the current control signal 330 from the processor 328 and supplying control information to emitter driving circuitry 334, which in turns drives the plurality of emitters 304 on the sensor 302 over conductors 316. In an embodiment, the emitter driving circuitry 334 drives sixteen (16) emitters capable of emitting light at sixteen (16) predefined wavelengths, although the circuitry 334 can drive any number of emitters. For example, the circuitry 334 can drive two (2) or more emitters capable of emitting light at two (2) or more wavelengths, or it can drive a matrix of eight (8) or more emitters capable of emitting light at eight (8) or more wavelengths. In addition, one or more emitters could emit light at the same or substantially the same wavelength to provide redundancy.

In an embodiment, the host instrument 320 communicates with the processor 328 to receive signals indicative of the physiological parameter information calculated by the processor 328. The host instrument 320 preferably includes one or more display devices 336 capable of providing indicia representative of the calculated physiological parameters of the tissue 306 at the measurement site. In an embodiment, the host instrument 320 can advantageously includes virtually any housing, including a handheld or otherwise portable monitor capable of displaying one or more of the foregoing measured or calculated parameters. In still additional embodiments, the host instrument 320 is capable of displaying trending data for one or more of the measured or determined parameters. Moreover, an artisan will recognize from the disclosure herein many display options for the data available from the processor 328.

In an embodiment, the host instrument 320 includes audio or visual alarms that alert caregivers that one or more physiological parameters are falling below or above predetermined safe thresholds, which are trending in a predetermined direction (good or bad), and can include indications of the confidence a caregiver should have in the displayed data. In further embodiment, the host instrument 320 can advantageously include circuitry capable of determining the expiration or overuse of components of the sensor 302, including, for example, reusable elements, disposable elements, or combinations of the same. Moreover, a detector could advantageously determine a degree of clarity, cloudiness, transparence, or translucence over an optical component, such as the detector 308, to provide an indication of an amount of use of the sensor components and/or an indication of the quality of the photo diode.

An artisan will recognize from the disclosure herein that the emitters 304 and/or the detector 308 can advantageously be located inside of the monitor, or inside a sensor housing. In such embodiments, fiber optics can transmit emitted light to and from the tissue site. An interface of the fiber optic, as opposed to the detector can be positioned proximate the tissue. In an embodiment, the physiological monitor accurately monitors HbCO in clinically useful ranges. This monitoring can be achieved with non-fiber optic sensors. In another embodiment, the physiological monitor utilizes a plurality, or at least four, non-coherent light sources to measure one or more of the foregoing physiological parameters. Similarly, non-fiber optic sensors can be used. In some cases the monitor receives optical signals from a fiber optic detector. Fiber optic detectors are useful when, for example, monitoring patients receiving MRI or cobalt radiation treatments, or the like. Similarly, light emitters can provide light from the monitor to a tissue site with a fiber optic conduit. Fiber optics are particularly useful when monitoring HbCO and HbMet. In another embodiment, the emitter is a laser diode place proximate tissue. In such cases, fiber optics are not used. Such laser diodes can be utilized with or without temperature compensation to affect wavelength.

Figure 4:
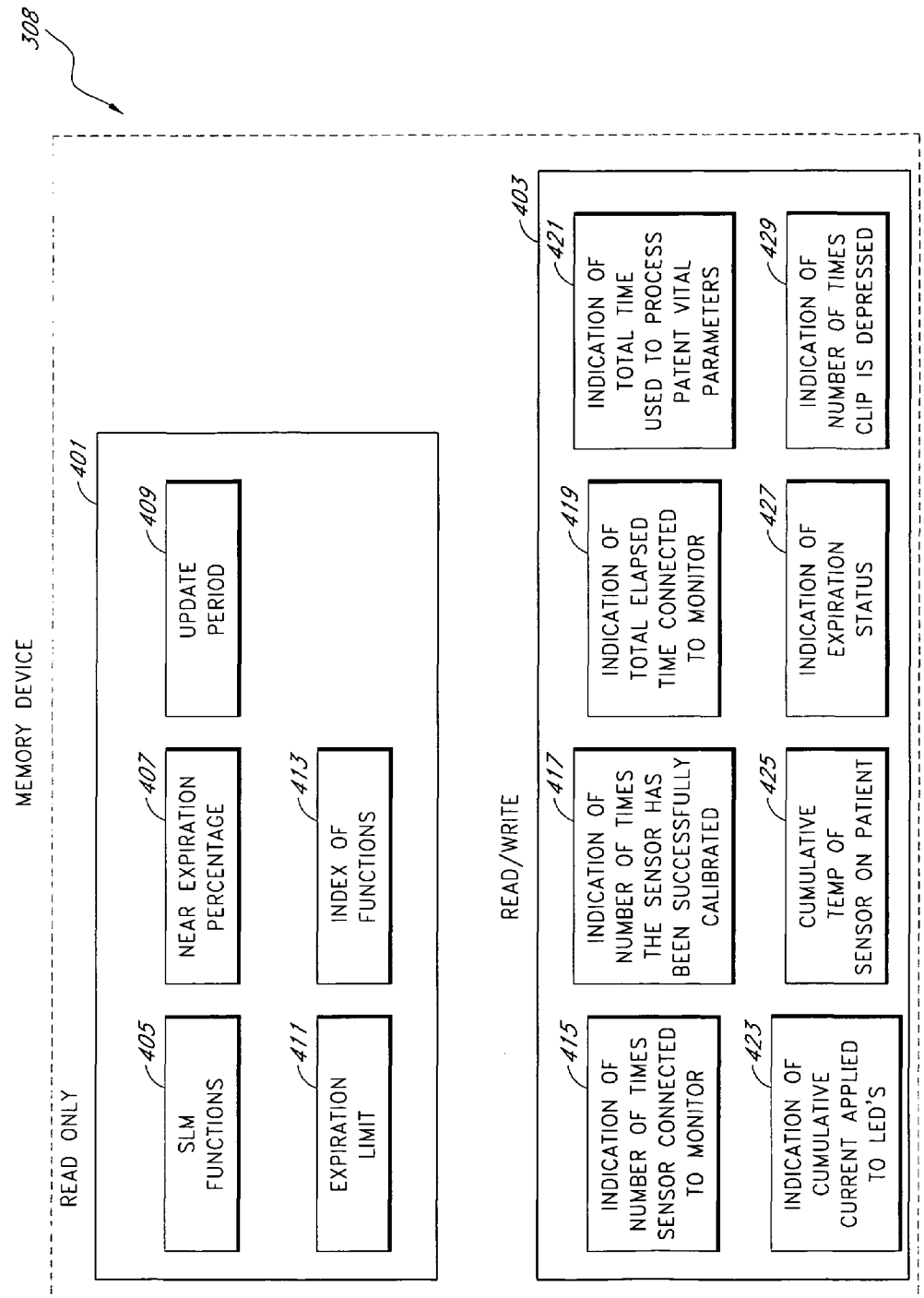
FIG. 4 illustrates a block diagram of the contents of one embodiment of a sensor memory.

FIG. 4 shows one embodiment of a memory device on the sensor 308. Memory device 308 has a read only section 401 and a read write section 403. One of ordinary skill in the art will understand that the read only and read write sections can be on the same memory or on a separate physical memory. One of ordinary skill in the art will also understand that the read only block 401 and the read write block 403 can consist of multiple separate physical memory devices or a single memory device. The read only section 401 contains read only information, such as, for example, sensor life monitoring functions (SLM) 405, near expiration percentage 407, update period 409, expiration limit 411, index of functions 413, sensor type or the like.

The read write section 403 contains numerous read write parameters, such as the number of times sensor is connected to a monitoring system 415, the number of times the sensor has been successfully calibrated 417, the total elapsed time connected to monitor system 419, the total time used to process patient vital parameters 421, the cumulative current applied to LEDs 423, the cumulative temperature of sensor on patient 425, the expiration status 427, and the number of times clip is depressed 429. Although described in relation to certain parameters and information, a person of ordinary skill in the art will understand from the disclosure herein that more or fewer read only and read/write parameters can be stored on the memory as is advantageous in determining the useful life of a sensor.

Figure 5:
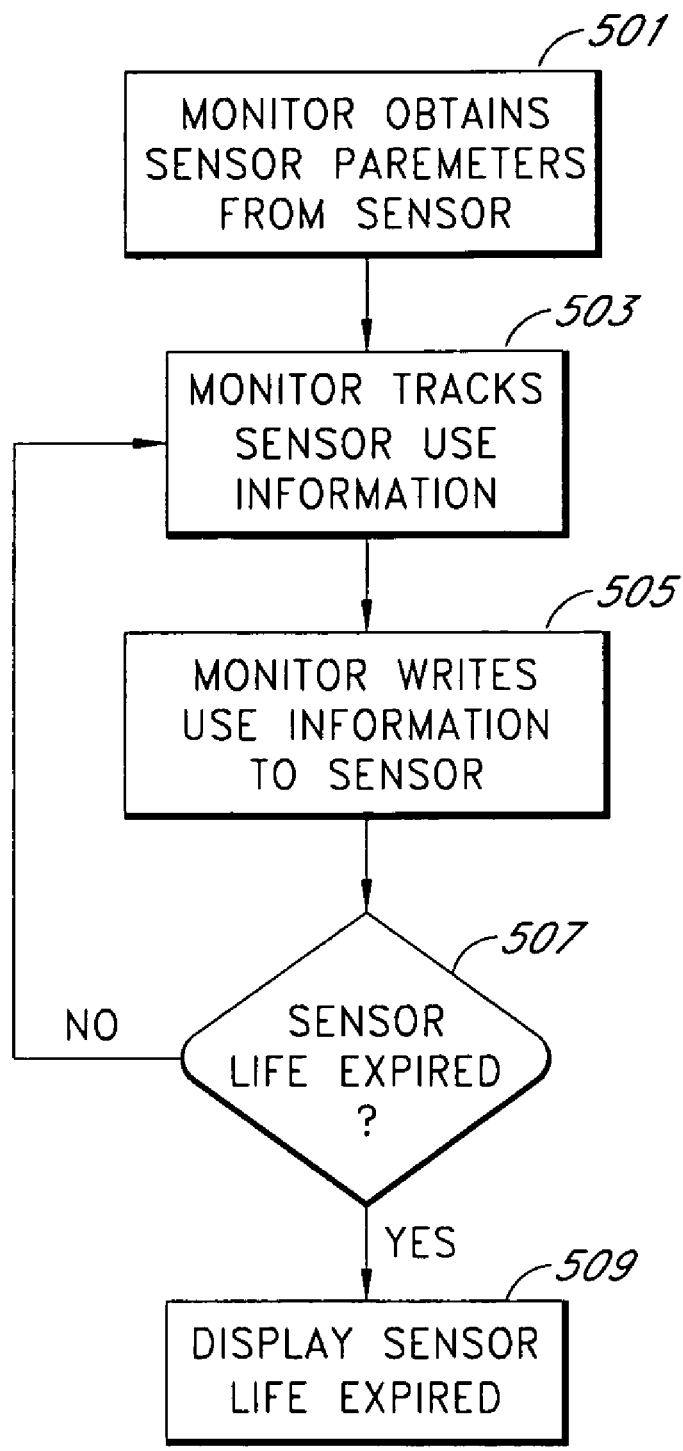
FIG. 5 illustrates a flowchart of one embodiment of a sensor life monitoring system.

FIG. 5 illustrates a flow chart of one embodiment of the read/write process between the monitor and the sensor. In block 501, the monitor obtains sensor parameters from the sensor. For example, in block 501, the monitor can access the read only section 401 of the memory device in order to obtain functions such as SLM functions 405, near expiration percentage 407, update period 409, expiration limit 411, and/or the index of functions 413. The monitor then uses these functions in block 503 to track sensor use information. In block 503, the monitor tracks sensor use information, such as, for example, the amount of time the sensor is in use, the amount of time the sensor is connected to a finger, the number of times the sensor opens and closes, the average temperature, the average current provided to the sensor, as well as any other stress that can be experienced by the sensor. The monitor then writes this use information on a periodic basis to the sensor at block 505. At decision block 507, the monitor decides whether or not the sensor life is expired based on the obtained parameters from the sensor and the use information. If the sensor's life has not expired at block 507, then the system returns to block 503 where the monitor continues to track sensor use information. If, however, at decision block 507 the monitor decides that the sensor life has expired, the monitor will display a sensor life expired at block 509.

Sensor use information can be determined in any number of ways. For example, In an embodiment, in order to determine the life of the emitters, the number of emitter pulses can be counted and an indication stored in memory. In an embodiment, the time period in which power is provided to the sensor is determined and an indication stored in memory. In an embodiment, the amount of current supplied to the sensor and/or LEDs is monitored and an indication is stored in memory. In an embodiment, the number of times the sensor is powered up or powered down is monitored and an indication is stored in memory. In an embodiment, the number of times the sensor is connected to a monitor is tracked and an indication is stored in memory. In an embodiment, the number of times the sensor is placed on or removed from a patient is monitored and an indication is stored in the memory. The number of times the sensor is placed on or removed from a patient can be monitored by monitoring the number of probe off conditions sensed, or it can be monitored by placing a separate monitoring device on the sensor to determine when the clip is depressed, opened, removed, replaced, attached, etc. In an embodiment, the average operating temperature of the sensor is monitored and an indication stored. This can be done, for example, through the use of bulk mass as described above, or through directly monitoring the temperature of each emitter, or the temperature of other parts of the sensor. In an embodiment, the number of different monitors connected to the sensor is tracked and an indication is stored in memory. In an embodiment, the number of times the sensor is calibrated is monitored, and an indication is stored in the memory. In an embodiment, the number of patients which use a sensor is monitored and an indication is stored. This can be done by, for example, by storing sensed or manually entered information about the patient and comparing the information to new information obtained when the sensor is powered up, disconnected and/or reconnected, or at other significant events or periodically to determine if the sensor is connected to the same patient or a new patient. In an embodiment, a user is requested to enter information about the patient that is then stored in memory and used to determine the useful sensor life. In an embodiment, a user is requested to enter information about cleaning and sterilization of the sensor, and an indication is stored in the memory. Although described with respect to measuring certain parameters in certain ways, a person of ordinary skill in the art will understand from the disclosure herein that various electrical or mechanical measurement can be used to determine any useful parameter in measuring the useful life of a sensor.

The monitor and/or the sensor determines the sensor life based on sensor use information. In an embodiment, the monitor and/or sensor uses a formula supplied by the sensor memory to measure the sensor life using the above described variables. In an embodiment, the formula is stored as a function or series of functions, such as SLM functions 405. In an embodiment, experimental or empirical data is used to determine the formula used to determine the sensor's life. In an embodiment, damaged and/or used sensors are examined and use information is obtained in order to develop formulas useful in predicting the useful sensor life.

In an embodiment, a formula or a set of formulas is stored in the monitor's memory. An indication of the correct formula or set of formulas to be used by the monitor is stored in the sensor. The indication stored on the sensor is read by the monitor so that the monitor knows which formula or series of formulas are to be used in order to determine the useful life of the sensor. In this way, memory space is saved by storing the functions or set of functions on the monitor's memory and only storing an indication of the correct function or functions to be used on the sensor memory.

In an embodiment, a weighted function or average of functions is determined based on the sensor/monitor configuration. For example, In an embodiment, the sensor life function is the sum of a weighted indication of use, for example, In an embodiment, the following sensor life function is used:

$$\sum_{1}^{n} f_{ij} c_j \qquad 1$$

where $f_{ij}$ refers to a function determined based on operating conditions and $c_j$ refers to an indication of sensor use. For example, the correct $f_{ij}$ can be determined from a table such as:

|    | Time$_1$ | Time$_2$ | Temp. | Current | Calibrations | Age | Model | ... | ... |
|----|----------|----------|-------|---------|--------------|-----|-------|-----|-----|
| F1 | $f_{1,1}$ | $f_{2,1}$ | $f_{3,1}$ | $f_{4,1}$ | $f_{5,1}$ | $f_{6,1}$ | $f_{7,1}$ | ... | ... |
| F2 | $f_{1,2}$ | $f_{2,2}$ | $f_{3,2}$ | $f_{4,2}$ | $f_{5,2}$ | $f_{6,2}$ | $f_{7,2}$ | ... | ... |
| F3 | $f_{1,3}$ | $f_{2,3}$ | $f_{3,3}$ | $f_{4,3}$ | $f_{5,3}$ | $f_{6,3}$ | $f_{7,3}$ | ... | ... |
| ... | ... | ... | ... | ... | ... | ... | ... | ... | ... |
| ... | ... | ... | ... | ... | ... | ... | ... | ... | ... |

Where $F_i$ refers the type of sensor and/or the type and number of parameters being monitored. For each different sensor and for each different parameter, a separate function is used in determining the useful life of a sensor. In an embodiment, the correct $F_i$ for a given sensor can be stored on the sensor memory. In an embodiment, all of the functions $f_{ij}$ for a sensor are stored in the sensor memory. In an embodiment, the entire table is stored in the sensor memory. $c_j$ can be determined from the monitored sensor parameters. For example, a $c_j$ for can be determined by counting the total time in use, averaging use time during certain parameters, squaring use time, etc. Thus a $c_j$ can be an indication of use. In an embodiment, the correct $c_j$ for the number of times the sensor has been turned on or off can be determined by the following formula:

$$e^{\frac{c}{100}} \qquad 2$$

where c is the number of times turned on or off.

In an embodiment, when the useful life of a sensor has been reached, the monitor or sensor sounds an alarm or gives a visual indication that the sensor is at the end of its life. In an embodiment, the monitor will give an indication that the sensor is bad. In an embodiment, the monitor will not output data. In an embodiment, an indication of the end of the sensor life is not given while the sensor is actively measuring vital signs. In an embodiment, the percent of life left in a sensor is indicated. In an embodiment, an estimated remaining use time is indicated. In an embodiment, an indication that the end of the sensor life is approaching is indicated without giving a specific percentage or time period.

Figure 6A:
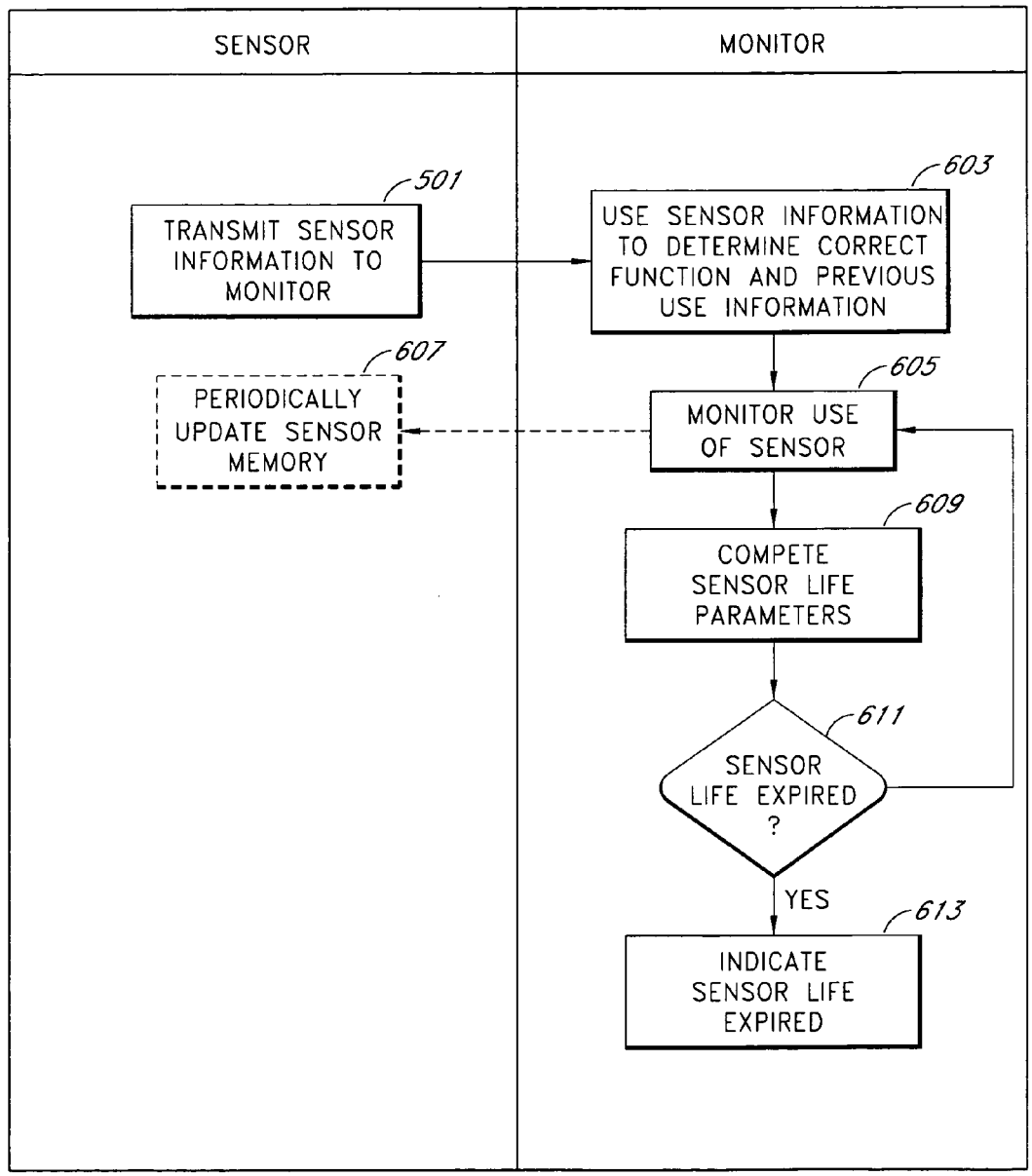
FIGS. 6A-6B illustrate flowcharts of embodiments of sensor life monitoring systems.
Figure 6B:
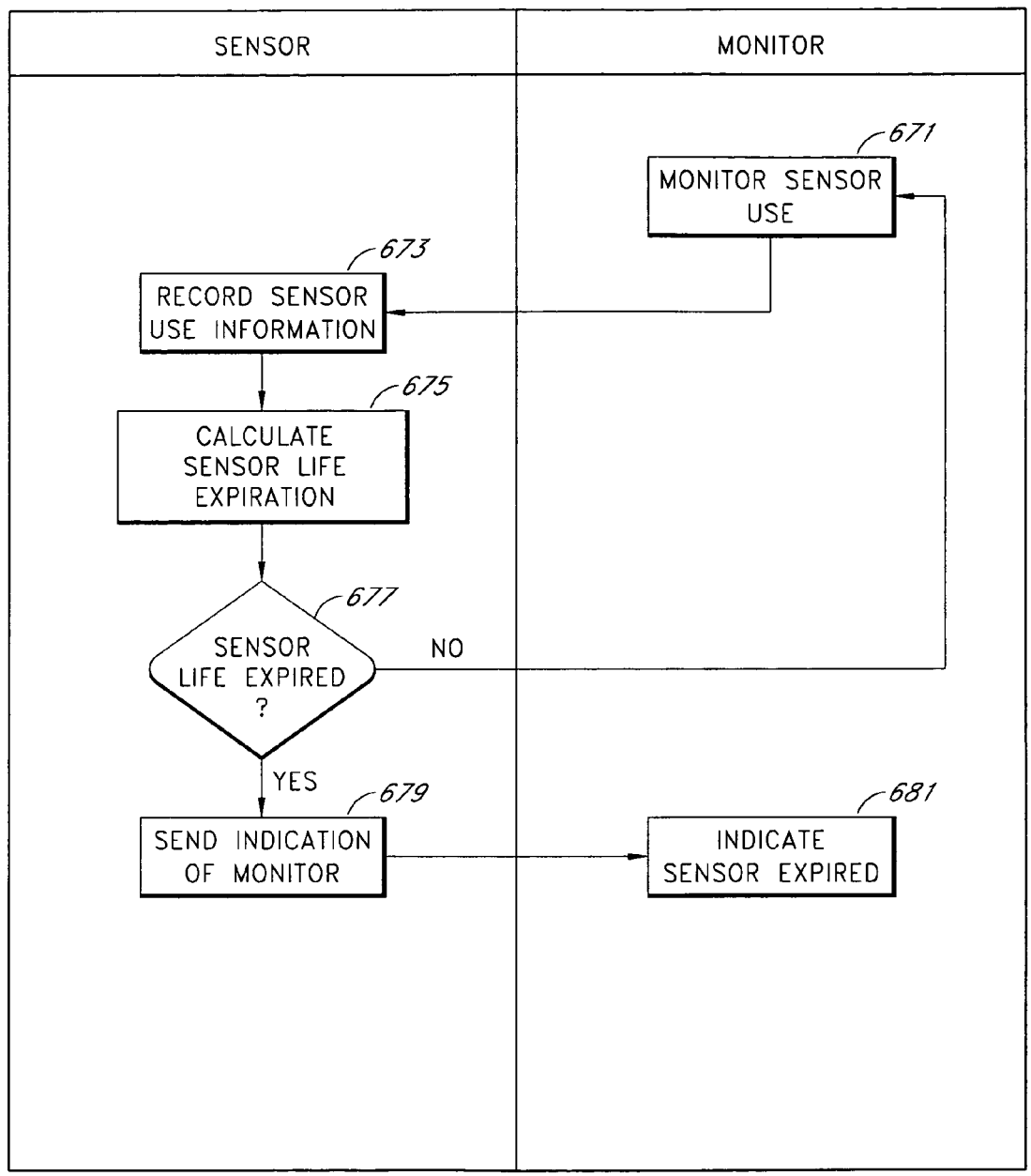

FIGS. 6A and 6B illustrate flowcharts of embodiments of sensor life monitoring systems. Referring to FIG. 6A, In an embodiment of a sensor life monitoring system, a sensor including a memory device is connected to a monitor. The sensor transmits sensor information to the monitor at block 601. The information can include one or more of a function, use parameters, expiration parameters, or any other sensor specific information useful in determining the life expiration of a sensor. At block 603, the sensor information is used to determine the correct function to use in determining the sensor expiration date. Any previous use information transmitted is also used during the monitoring process. At block 605, the patient monitor monitors the sensor use. Optionally, the monitor periodically writes updated use information to the sensor at block 607 or In an embodiment, the use information is written once at the end of a monitoring cycle. At block 609, the monitor computes sensor life parameters and sensor life expiration. The system then moves onto decision block 611 where it is determined whether the sensor life has expired. If the sensor life has expired, then the system moves to block 613 where an indication of the sensor life expiration is given. If the sensor life has not expired at decision block 611, then the system returns to block 605, where sensor use is monitored.

FIG. 6B illustrates a flowchart where the sensor life is calculated on the sensor instead of the monitor. At block 671, the patient monitor monitors sensor use. The use information is supplied to the sensor at block 673, the use information is recorded. At block 675, the sensor calculates the sensor life expiration. The system then moves onto decision block 677. At decision block 677, if the sensor has expired, the system moves onto block 679, where the sensor sends an expiration indication to the monitor and the monitor indicates the sensor expiration at block 681. If, however, at block 671 the sensor has not expired, the system returns to block 671 where the sensor use is monitored.

Figure 7:
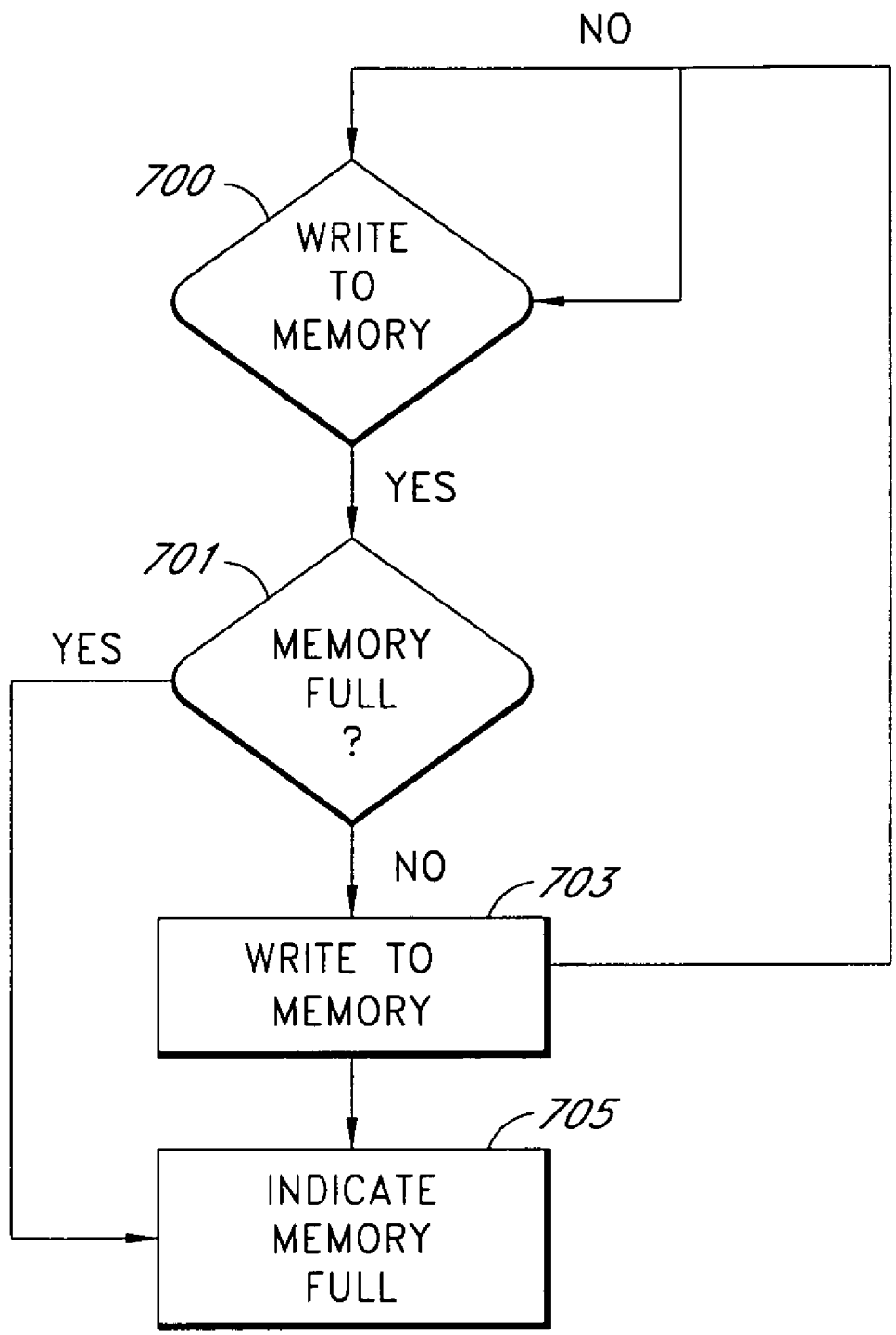
FIG. 7 illustrates a flowchart of one embodiment of a sensor life monitoring system.

FIG. 7 illustrates a flowchart of an embodiment of a system for measuring the life of a sensor. In the course of monitoring a patient, information is written on the EPROM. Because the EPROM is finite in the amount of information it can hold, at some point, the EPROM becomes full. When the EPROM becomes full, the sensor will need to be replaced. Thus, an EPROM full signal indicates that the life span of the sensor has expired. The EPROM's memory capacity can be chosen to so as to estimate the life of the sensor. In addition, the monitor can be programmed to write to the sensor at set intervals so that after a predictable period of time, the EPROM's memory will be full. Once the EPROM is full, the monitor gives an audio and/or visual indication that the sensor needs to be replaced.

Referring to FIG. 7, the patient monitoring system determines whether to write to the sensor EPROM at block 700. If information is not to be written to the EPROM at block 700, then the system continues at block 700. If information is to be written to the EPROM at block 700, then the system continues to block 701, where the system determines if the EPROM is full. If the EPROM is full, then the system moves to block 703, where the system writes information to the EPROM. Once the information has been written, the system returns to block 700 where it waits until information is to be written to the EPROM. If at block 701, the system determines that the EPROM is full, then the system moves to block 703, where an indication is given to the user that the sensor needs to be replaced.

In an embodiment, the sensor can be refurbished and used again. For example, if the memory used is an erasable memory module, then the sensor's memory can be erased during the refurbishment process and the entire sensor can be used again. In an embodiment, each time part or all of the memory is erased, an indicator of the number of times the memory has been erased is stored on the memory device. In this way, an indication of the number of refurbishments of a particular sensor can be kept. If a write only memory is used, then parts of the sensor can be salvaged for reuse, but a new memory module will replace the used memory module. In an embodiment, once the sensor memory is full, the sensor is discarded.

In an embodiment, various parts of used sensors can be salvaged and reused. In an embodiment, the sensor keeps track of various use information as described above. The sensor memory can then be reviewed to see which parts of the used sensor can be salvaged based on the use information stored in the memory. For example, In an embodiment, an indication of the number of times the clip is depressed is stored in memory. A refurbisher can look at that use information and determine whether the mechanical clip can be salvaged and used on a refurbished sensor. Of course, the same principals apply to other aspects of the sensor, such as, for example, the LEDs, the cables, the detector, the memory, or any other part of the sensor.

Although the foregoing invention has been described in terms of certain preferred embodiments, other embodiments will be apparent to those of ordinary skill in the art from the disclosure herein. For example, although disclosed with respect to a pulse oximetry sensor, the ideas disclosed herein can be applied to other sensors such as ECG/EKG sensor, blood pressure sensors, or any other physiological sensors. Additionally, the disclosure is equally applicable to physiological monitor attachments other than a sensor, such as, for example, a cable connecting the sensor to the physiological monitor. Additionally, other combinations, omissions, substitutions and modifications will be apparent to the skilled artisan in view of the disclosure herein. It is contemplated that various aspects and features of the invention described can be practiced separately, combined together, or substituted for one another, and that a variety of combination and subcombinations of the features and aspects can be made and still fall within the scope of the invention. Furthermore, the systems described above need not include all of the modules and functions described in the preferred embodiments. Accordingly, the present invention is not intended to be limited by the recitation of the preferred embodiments, but is to be defined by reference to the appended claims.

What is claimed is:

1. A reusable noninvasive physiological sensor configured to store sensor use information comprising:
a first and second emitter configured to emit light of at least two wavelengths through tissue;
a detector configured to sense the light after it has passed through the tissue and to generate a signal indicative of the sensed light;
a memory device configured to store at least one indication of sensor use information and at least one indication of a function to be used by a separately housed patient monitor in determining the useful life of the sensor; and a communication port configured to communicate at least the signal and information stored on the memory with the separately housed patient monitor, wherein the at least one indication of the function provides at least one weight, and the separately housed patient monitor configured to use the at least one weight to weight at least one of the at least one indication of sensor use information greater than at least a second indication of sensor use information in the determination of the useful life of the sensor.

2. The sensor of claim 1, wherein the memory device comprises a read only portion and a read/write portion.

3. The sensor of claim 2, wherein the indication of the function is stored in the read only portion and the indication of sensor use information is stored in the read/write portion.

4. The sensor of claim 1, wherein the memory device is comprised of a plurality of memory devices.

5. The sensor of claim 1, wherein the indication of the sensor use information comprises an indication of one or more of an age of the sensor, a use time of the sensor, a current supplied to the sensor, a temperature of the sensor, a number of times the sensor is depressed, a number of times the sensor is calibrated, and a number of times the sensor is powered up.

6. The sensor of claim 5, wherein the monitor tracks the use information and sends an indication of the use information to the sensor for storage in the memory.

7. A method of determining the useful life of a physiological sensor comprising a memory device comprising:
using a physiological sensor comprising a memory device to obtain physiological information;
monitoring the use of the sensor using a separately housed patient monitor;
storing a plurality of indications of use of the sensor on the memory device; and
using the separately housed patient monitor to determine when the useful life of the sensor has been exceeded by using at least two of the plurality of indications of use of the sensor stored in the memory device and one or more indications of mathematical functions selected from a plurality of indications of mathematical functions stored in the memory device, wherein
the plurality of indications of use of the sensor comprises at least a first indication of use of the sensor and a second indication of use of the sensor, and
at least one of the one or more indications of mathematical functions weights the first indication of use of the sensor greater than the second indication of use of the sensor.

8. The method of claim 7, wherein a plurality of mathematical functions is stored on a patient monitor.

9. The method of claim 8, wherein the sensor is used to select one or more of the plurality of mathematical functions.

10. The method of claim 8, wherein the one or more of the plurality of mathematical functions is derived from use data.

11. The method of claim 8, wherein at least one of the plurality of indications of use is used to select one or more of the plurality of the one or more mathematical functions.

12. The method of claim 8, wherein one or more of the plurality of mathematical functions comprises two or more mathematical functions.

13. The method of claim 7, wherein at least one of the plurality of indications of use of the sensor comprises an indication of one or more of an age of the sensor, a use time of the sensor, a current supplied to the sensor, a temperature of the sensor, a number of times the sensor is depressed, a number of times the sensor is calibrated, and a number of times the sensor is powered up.

14. The method of claim 7, wherein the one or more indications of mathematical functions are mathematical functions.

15. The method of claim 10, wherein the use data is obtained from used sensors.

16. The method of claim 15, wherein used sensors are used on patients.

17. The method of claim 7, wherein the physiological sensor is one or more of a blood oxygen sensor, a blood pressure sensor, and an ECG sensor.

18. The method of claim 7, further comprising determining if at least one portion of the sensor can be reused.

19. The method of claim 18, further comprising reusing the at least one portion of the sensor.

20. The method of claim 19, wherein reusing comprises producing a refurbished sensor comprising the at least one part of the sensor.

21. The method of claim 18, further comprising analyzing at least one of the plurality of indications of use of the sensor to determine an extent of use of the sensor.

22. The method of claim 20, further comprising storing reuse information on the refurbished sensor.

23. A method of indicating when a physiological sensor including a sensor memory module needs to be replaced comprising:
emitting light from a light emitting element using at least one emitter drive signal conductor that is coupled with a separately housed patient monitor;
detecting light from the light emitting element after it has been attenuated by tissue;
storing a first indication of sensor use information on a sensor memory module on the sensor;
determining, using the separately housed patient monitor in communication with the sensor, when the useful life of the sensor has been exceeded using an indication of a mathematical function stored in the sensor memory module, wherein the mathematical function weights the first indication of sensor use information greater than a second indication of sensor use information; and
indicating that the sensor needs be replaced.

24. The method of claim 23, further comprising storing information at predetermined time intervals.

25. The method of claim 24, wherein information comprises usage information.

26. The method of claim 23, wherein the mathematical function takes into account two or more different parameters in determining the useful life of the sensor.

27. The sensor of claim 1, wherein the indication of a function is a mathematical function.

28. A method of determining the useful life of a physiological sensor comprising a memory device comprising:
using a physiological sensor comprising a memory device to obtain physiological information;
monitoring the use of the physiological sensor using a separately housed patient monitor;
storing at least a first indication of use of the physiological sensor and a second indication of use of the physiological sensor on the memory device;
assigning a first weighted value to the first indication of use and a second weighted value to the second indication of use; and
determining when the useful life of the physiological sensor has been exceeded by using at least the first indication of use, the second indication of use, the first weighted value, the second weighted value, and one or more mathematical functions.

29. The method of claim 28, wherein the first weighted value and the second weighted value are assigned according to a predetermined method.

30. The method of claim 28, wherein the first weighted value is greater than the second weighted value.

31. The method of claim 28, wherein the one or more mathematical functions are stored in the memory device of the physiological sensor.

32. The method of claim 28, wherein the one or more mathematical functions are stored in the separately housed patient monitor.

33. The method of claim 32, wherein determining the useful life of the physiological sensor further comprises using one or more indications of a mathematical function stored in the memory device of the physiological sensor, wherein the one or more indications of a mathematical function stored in the memory device of the physiological sensor correspond to the one or more mathematical functions stored in the separately housed patient monitor.

* * * * *